United States Patent
Fischer et al.

(10) Patent No.: US 7,300,748 B2
(45) Date of Patent: Nov. 27, 2007

(54) METHOD FOR ENHANCING STAINING OF MICROORGANISMS

(75) Inventors: Timothy Fischer, Raleigh, NC (US); Walter Sherman, Oro Valley, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 11/172,057

(22) Filed: Jun. 29, 2005

(65) Prior Publication Data

US 2005/0239148 A1    Oct. 27, 2005

Related U.S. Application Data

(62) Division of application No. 10/134,575, filed on Apr. 29, 2002.

(51) Int. Cl.
*A01N 1/00*    (2006.01)
(52) U.S. Cl. ....................................... 435/1.1
(58) Field of Classification Search ................. 435/1.1
See application file for complete search history.

(56) References Cited

U.S. PATENT DOCUMENTS

| 5,853,748 A | 12/1998 | New |
| 2001/0050810 A1 | 12/2001 | Lorincz |

FOREIGN PATENT DOCUMENTS

WO    WO96/06182    2/1996

OTHER PUBLICATIONS

Kabasawa et al (Japanese Journal of Ophthamology vol. 21, No. 3, pp. 348-354, 1977).*
Anim, et al, "Assessment of Different Methods for Staining Helicobacter pylori in Endoscopic Gastric Biopsies," ACTA Histochem., Urban & Fischer Verlag, vol. 102, pp. 129-137, (2000).
Leung, et al, "Rapid Staining Method for Helicobacter pylori in Gastric Biopsies," Journal of Histotechnology, vol. 19 (No. 2), pp. 131-132, (1996).
Vartanian, et al, "A Novel Alcian Yellow-Toluidine Blue (Leung) Stain for Helicobacter Species: Comparison with Standard Stains, a Cost-Effectiveness Analysis, and Supplemental Utilities," Modern Patholoy, vol. 11 (No. 1), pp. 72-78, (1998).
Llewellyn B., "Alcian Yello", URL <http://members.pgonline.com/~bryand/StainsFile/dyes/12840.html.

* cited by examiner

*Primary Examiner*—Mark Navarro
(74) *Attorney, Agent, or Firm*—Huw R. Jones

(57) ABSTRACT

The invention is directed to a method and composition of matter for enhancing the staining of tissue or features of interest therein by applying an effective amount of a bile salt in combination with a special stain to a tissue suspected of harboring a microorganism or other feature of diagnostic interest. The particular invention herein is directed to detecting *H. pylori*, the microorganism responsible for gastrointestinal ulcers. The composition of matter is a sensitizer for Alcian Yellow stain.

6 Claims, 1 Drawing Sheet
(1 of 1 Drawing Sheet(s) Filed in Color)

Without SDC

With SDC

METHOD FOR ENHANCING STAINING OF MICROORGANISMS

CROSS REFERENCE TO RELATED APPLICATIONS

This application is a divisional of U.S. patent application Ser. No. 10/134,575 filed Apr. 29, 2002, the contents of which are hereby incorporated by reference in their entirety into the subject application.

BACKGROUND

1. Field of the Invention

This invention is in the general field of histology, in particular the invention is an improved composition and method for staining microorganisms.

2. Description of Related Art

Histology is the practice of examination and classification of tissue to aid in diagnosis of a disease or condition expressed in the morphology of the affected tissue. The practice of staining tissue or features of tissues with a visualizing agent to visualize or detect them, and thus provide a scientific basis for diagnosing a patient, is a very old art, going back over one hundred years. Histology can be divided into three basic practice areas: immunohistochemistry (use of antibodies to visualize tissue structures), in situ hybridization (use of DNA/RNA probes to detect) or special stains (chemical staining of tissue). Special stains is the term given to a collection of chemically-based stains that have been developed in response to difficult to stain tissue types, unusual diseases, infectious diseases or other non-typical situations affecting the tissue.

The staining of histologic sections of tissue for the identification of *H. pylori* using a combination of Alcian Yellow and Toluidine Blue was published by Leung et al. (Leung, J K, Gibbob, K J, Vartanian, R K, "Rapid staining method for *Heliobacter pylori* in gastric biopsies," J. Histol. 19:131-132 (1996).

SUMMARY OF THE INVENTION

The invention is directed to a method and composition of matter for enhancing the staining of tissue or features of interest therein by applying an effective amount of a bile salt in combination with a special stain to a tissue suspected of harboring a microorganism or other feature of diagnostic interest. The particular invention herein is directed to detecting *H. pylori*, the microorganism responsible for gastrointestinal ulcers.

The composition of matter is a sensitizer for Alcian Yellow stain.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE PREFERRED EMBODIMENTS

Figure 1:
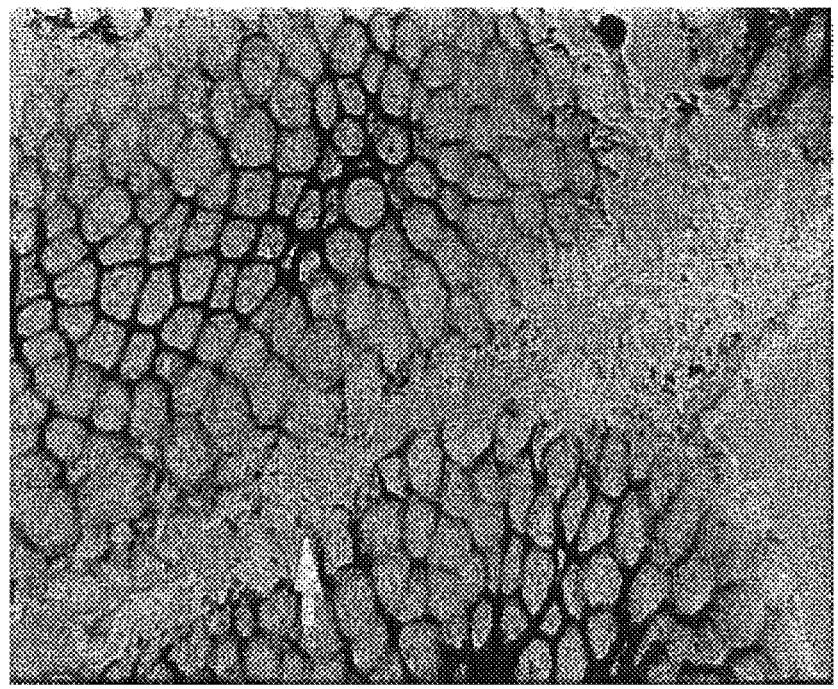
FIG. 1 includes two color pictures of a section of tissue on a slide stained using the recipe and Alcian Yellow sensitizer of the present invention. The top picture is a tissue section not stained using the sensitizer, and the bottom picture is of a tissue section wherein the recipe included in addition the step of using the sensitizer.
Figure 1:
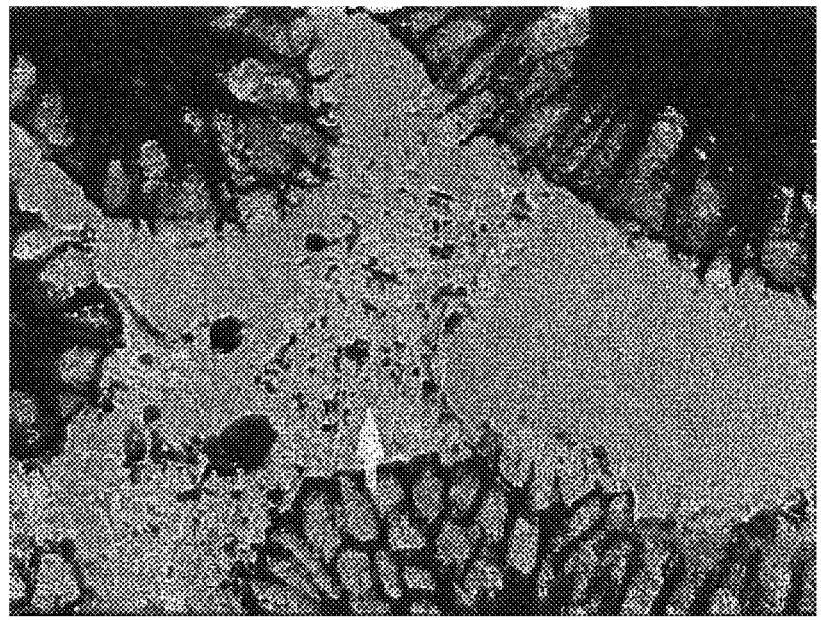

The staining of histologic sections for the identification of *Heliobactor pylori* using a combination of Alcian Yellow and Toluidine Blue was published by Leung et al (Leung, J K, Gibbon, K J, Vartanian, R K: Rapid staining method for *Heliobacter pylori* in gastric biopsies. J. Histol 19:131-132, 1996). The combination normally results in *H. Pylori* being stained blue, the mucin yellow and the background blue. We were able to replicate the results of this procedure using manual methods, but were unable to achieve good staining of the *H. pylori* organisms when the procedure was automated on the NexES® Special Stains instrument (Ventana Medical Systems, Inc., Tucson, Ariz.).

To achieve a stable Toluidine stain solution, the published formulation was modified. Instead of adding a dilute solution of sodium hydroxide to the diluted Toluidine Blue stock solution just prior to use, we dispensed a solution of 0.025 M sodium borate, pH 9.30+/−0.05 to the tissue on the slide, followed by dispensing the Toluidine Blue dye. We used this same technique previously with Toluidine Blue solution applied as a counterstain in the automated AFB II Staining kit (Ventana Medical Systems, Tucson, Ariz.). In an analysis of this data, the inventors concluded that the nonionic detergent (Tween 20) used in the Water Wash solution interfered with binding of the Toluidine Blue dye to the microorganisms. We modified the borate buffer solution to add a series of compounds that we suspected might neutralize the effect of the nonionic detergent. Surprisingly, only one compound, sodium desoxycholate (Sigma-Aldrich, Cat. No. D6750), achieved the desired effect, and the effect was shown to be optimum at a SDC concentration between 0.32%-0.64%. We chose the near midpoint concentration of 0.05% SDC for further experiments.

The temperature of the NexES Special Stains instrument was reduced to ambient by leaving the heat turned off, and the concentration of Alcian Yellow and Toluidine dyes was optimized for the lower temperature (pp 16-23, AY notebook 3, attached). An experiment was then performed to test the optimized reagents against three (3) tissues cut at 3, 4 and 5 micron thicknesses. The optimized reagent performed satisfactorily in comparison to manual stains.

A "special stain" as defined herein is any chemically-based stain useful for histological analysis that is not an immunohistochemical stain, or an in situ hybridization stain. A representative listing of such stains may be found in "Theory and Practice of Histological Techniques," Bancroft, John D., Stevens, Alan, eds., Fourth Ed. (1996), Churchill Livingstone Press, New York.

The invention is directed to a method for enhancing the staining of tissue or features of interest therein by applying an effective amount of a bile salt in combination with a special stain to a tissue suspected of harboring a microorganism or other featue of diagnostic interest. The particular invention herein is directed to detecting *H. pylori*, the microorganism responsible for gastrointestinal ulcers. On the NexES Special Stains instrument, the method is practiced according to the following general recipe, all of which are carried out at room temperature:

1) The slide with tissue adhered to it was rinsed using a solution of Tween 20.
2) 200 uL of Alcian Yello Oxidizer was added to the slide, and it was incubated for four minutes.

-continued

3) Liquid Coverslip ™ ("LCS") was applied.
4) Rinsed slide.
5) Adjusted slide volume and applied LCS.
6) Incubated for 4 more minutes.
7) Rinsed.
8) Applied Volume Adjust, and then 200 uL Alcian Yellow Clarifier.
9) Incubated for eight minutes, and the applied LCS.
10) Rinsed.
11) Adjusted slide volume, applied LCS
12) Incubated four minutes.
13) Rinsed slide.
14) Applied volume adjust, then added 200 uL of Alcian Yellow Stain.
15) Incubated four minutes, applied LCS.
16) Rinsed.
17) Volume adjusted, and added 200 uL Alcian Yellow Sensitizer.
18) Incubated four minutes, applied LCS.
19) Volume adjusted, and then added 200 uL Alcian Yellow Toluidine Blue.
20) Incubated four minutes, blowoff.
21) Rinsed.

The invention described herein is called "Alcian Yellow Sensitizer" and comprises 1.9% sodium borate decahydrate and 0.5% sodium desoxycholate, in aqueous solution (DI water). The preferred range of concentration for the sodium desoxycholate is 0.32% to about 0.64%. 1 N NaOH is added to balance pH to between 9.25 and 9.35. All of the following are available from Ventana Medical Systems, Tucson, Ariz.: Alcian Yellow Toluidine Blue, P/N 10551. Alcian Yellow Stain, P/N 10549. Alcian Yellow Oxidizer, P/N 10514. Alcian Yellow Clarifier, P/N 10012. Rinse and volume adjust solutions are stock solutions, also available from Ventana.

Results are best seen in relation to FIG. 1. FIG. 1 includes two color pictures of a section of tissue on a slide stained using the recipe and Alcian Yellow sensitizer of the present invention. The top picture is a tissue section stained without using the sensitizer, and the bottom picture is of a tissue section wherein the recipe included in addition the step of using the sensitizer. The arrows point to areas where *H. pylori* are present. The bottom picture shows a remarkable enhancement of staining in the small blue dots, which is the *H. pylori* microorganism.

We claim:

1. A method of enhancing the staining of whole tissue or features of diagnostic interest therein for subsequent microscopic viewing comprising applying an effective amount of sodium desoxycholate and Alcian Yellow to a whole tissue suspected of harboring a microorganism or other feature of diagnostic interest.

2. The method of claim 1 wherein said sodium desoxycholate has a concentration range of from about 0.32% to about 0.64%.

3. The method of claim 1 wherein said tissue suspected of harboring a microorganism comprises gastric tissue.

4. The method of claim 1 wherein said microorganism comprises *H. pylori*.

5. A method of enhancing the staining of whole gastric tissue or features of diagnostic interest therein for subsequent microscopic comprising applying an effective amount of sodium desoxycholate and Alcian Yellow to whole gastric tissue suspected of harboring the *H. pylori* microorganism.

6. The method of claim 5 wherein said sodium desoxycholate has a concentration range of from about 0.32% to about 0.64%.

* * * * *